United States Patent [19]

Birnbaum et al.

[11] 4,311,707
[45] Jan. 19, 1982

[54] PROCESS FOR TOPICALLY PRODUCING CUTANEOUS VASODILATION FOR THE TREATMENT OF VASOSPASTIC OR ISCHEMIC CONDITIONS

[75] Inventors: Jay E. Birnbaum, Pomona, N.Y.; Luc Van Humbeeck, Wauthier-Braine; Franz Dessy, Braine Le Chateau, both of Belgium

[73] Assignee: American Cyanamid Company, Stamford, Conn.

[21] Appl. No.: 11,364

[22] Filed: Feb. 12, 1979

[51] Int. Cl.$^3$ .......................................... A61K 31/215
[52] U.S. Cl. ................................... 424/305; 424/311; 424/317; 424/331
[58] Field of Search ............... 424/305, 317, 311, 331; 560/121

[56] References Cited

U.S. PATENT DOCUMENTS 3,551,554 12/1970 Herschler ................................ 424/7
4,131,738 12/1978 Smith .................................... 560/121
4,158,667 6/1979 Axen .............................. 560/121 X

OTHER PUBLICATIONS

Lowe and Stoughton—J. of Investigative Dermatology, 68:134–137, 1977.
Merck Manual—10th Ed., 1961, pp. 238, 239, 1426–1429.
Conway et al.—Chem. Abst., vol. 83 (1975), p. 91,369e.
Harrison et al.—Chem. Abst., vol. 83 (1975), p. 53,742p.
Williams et al.—Chem. Abst., vol. 88 (1978), p. 183,486x Primary Examiner—Leonard Schenkman

[57] ABSTRACT

This application discloses a process for producing cutaneous vasodilation which comprises the topical administration to an individual with a vasospastic or ischemic condition of an effective dosage of a prostaglandin vasodilator of the natural or synthetic prostaglandin analogs of the PGE, PGA, or PGF$_\beta$ types.

9 Claims, 2 Drawing Figures

PROCESS FOR TOPICALLY PRODUCING CUTANEOUS VASODILATION FOR THE TREATMENT OF VASOSPASTIC OR ISCHEMIC CONDITIONS

DESCRIPTION OF THE PRIOR ART

Peripheral vascular diseases include a variety of arteriospastic and occlusive disorders. The major difficulty associated with the treatment of such diseases with systemic vasodilators is the inability of these drugs to produce a specific vasodilation in critical ischemic areas. The generalized vasodilation induced by systemic vasodilators may actually exacerbate the ischemia produced by a peripheral vascular disease by shunting the blood into non-ischemic areas.

Non-specificity of activity is also responsible for the numerous side-effects associated with prior art peripheral vasodilators. For example, central sympathetic inhibitors such as reserpine and methyl dopa cause bradycardia, nasal congestion, impotence, depression, drug fever, and hepatic disfunction; $\alpha$-adrenergic receptor blocking agents such as tolazoline, azapetine and phenoxybenzamine cause nasal congestion, aggravation of angina, hypotension, headache and tachycardia; $\beta$-adrenergic stimulating agents such as nylidrin and isoxsuprine cause anxiety, palpitations, aggravation of angina and tachycardia; while direct smooth muscle relaxants such as ethanol, papaverine and cyclandelate cause intoxication, respiratory depression, exacerbation of peptic ulcer, nausea, dizziness and headache.

The potent vasodilator activity of the E-type prostaglandins is well recognized. See, e.g. Bergstrom, S. et. al., The Prostaglandins: A Family of Biologically Active Lipids, *Pharm. Rev.* 20: 1–48, 1968. The systemic administration of the PGE type prostaglandins however, is associated with untoward side effects on many organ systems, while intradermal injection elicits an erythematous response with swelling, hyperalgia and at higher dosages, wheal and flare. U.S. Pat. No. 4,009,282 discloses the use of the PGE series of prostaglandins and their esters to treat proliferating skin diseases.

It has been recently reported that 15(S)-15-methyl $PGE_2$ methyl ester induces an erythema upon topical administration to the skin of a hairless mouse, while $PGE_2$ itself was ineffective in illiciting such a response. See, Lowe, N.J. and Stoughton, R.B., Effects of Topical Prostaglandin $E_2$ Analog on Normal Hairless Mouse Epidermal DNA Synthesis, *The Journal of Investigative Dermatology* 68: 134–137, 1977. Although Lowe and Stoughton disclose the administration of 15(S)-15-methyl $PGE_2$ methyl ester to topically induce an erythema, they do not disclose a method of employing topical formulations of this prostaglandin for a therapeutic purpose, such as for the treatment of peripheral vascular disorders. Nor do they disclose a method of producing cutaneous, vasodilation without associated inflammatory changes.

BRIEF DESCRIPTION OF THE INVENTION

It is an object of the present invention to provide a method for producing cutaneous vasodilation free of the difficulties associated with the administration of the prior art systemic vasodilators discussed above. More specifically, it is an object of the present invention to provide a method wherein vasodilators are applied topically by direct application to the surface of the skin or by local injection to the site of an ischemic or vasospastic condition such that the activity of the drug is controlled and restricted to the site of administration.

It is also an object of the present invention to provide a method of treating peripheral vascular diseases of the vasospastic and occulusive types free of the undesirable side-effects which accompany the administration of systemic vasodilators currently employed to treat such diseases.

In accordance with the foregoing objectives the present invention provides a method of producing cutaneous vasodilation which comprises the topical administration to an individual with a vasospastic or ischemic condition of an effective dosage of a prostaglandin compound of the natural or synthetic prostaglandin analogs of the PGE, PGA, or $PGF_\beta$ types.

DETAILED DESCRIPTION OF THE INVENTION

Figure 1:
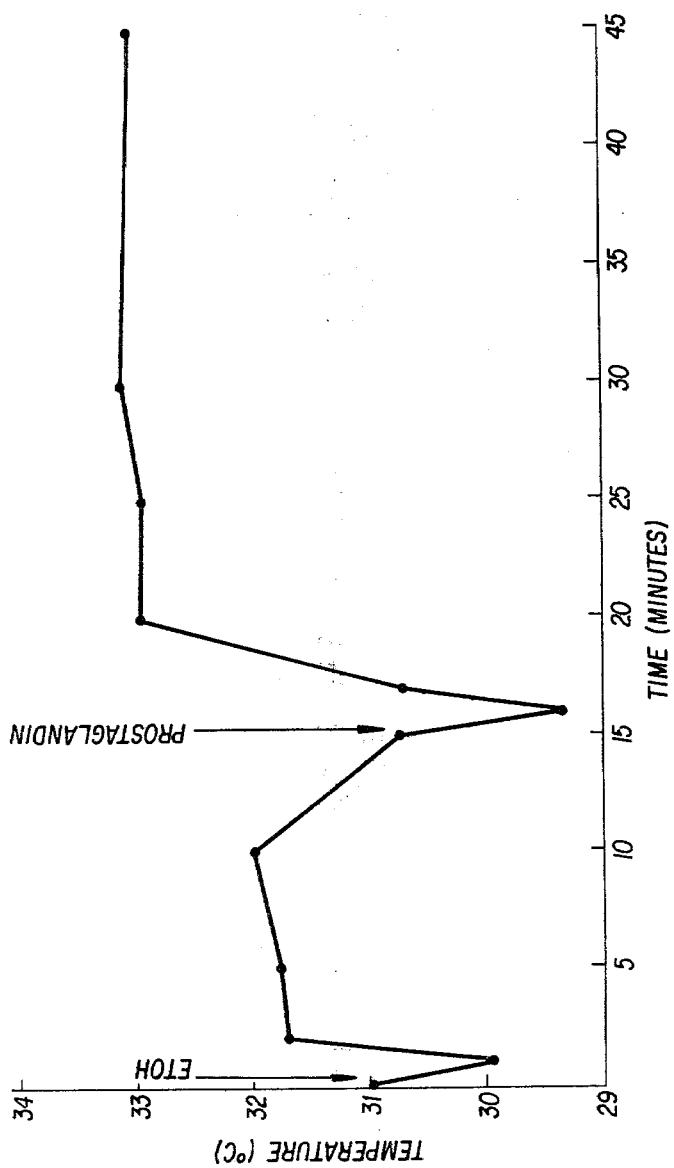

This invention relates to compounds and pharmaceutical preparations which when applied topically or by injection produce a distinct increase in peripheral (cutaneous and deep vessel) circulation. The intense and persistent vasodilation induced by the administration to the skin, of the prostaglandins of the natural or synthetic analogs of the PGE, PGA and $PGF_\beta$ prostaglandin types, renders these compounds especially useful for the treatment of peripheral vascular diseases of the arteriospastic and occlusive types. Thus, the prostaglandin compounds and compositions containing them disclosed herein are useful for the treatment of diseases such as, Buerger's disease, livedo reticularis, acrocyanosis, atheroclerosis, frostbite, impending gangrene, and other ischemic disorders. Moreover, the ability of the prostaglandins of the instant invention to increase peripheral circulation renders them useful to enhance the rate of healing of wounds, ulcers, infections and proliferative and inflammatory skin lesions including atopic dermatitis, acne and psoriasis; to treat impotency; or to enhance the rate of absorption of pharmaceutically active agents. In addition, topical preparations containing the active prostaglandins of the instant invention may be employed to improve skin color and to promote blush.

The prostaglandins utilized herein are the natural or synthetic analogs of the PGE, PGA and $PGF_\beta$ prostaglandin types which may be represented by the following general formula:

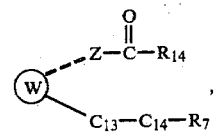

the mirror image thereof, and the racemic mixture thereof wherein W is selected from the group consisting of:

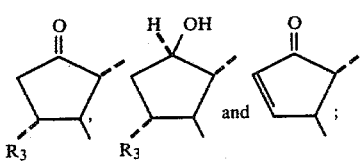

wherein $R_3$ is selected from the group consisting of hydrogen, hydroxyl and $HOCH_2CH_2S-$; Z is selected from the group comprising $-(CH_2)_6-$,

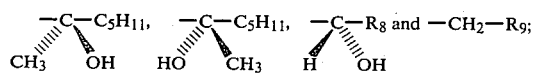

$-(CH_2)_m-S-CH_2-$, $-(CH_2)_m-O-CH_2-$, wherein n and m have the value of from 3 to 5 inclusive; $R_{14}$ is selected from the group consisting of hydroxyl, $C_1-C_6$ alkoxy, $-CH_2OH$ or $-CH_2OR_{15}$ wherein $R_{15}$ is $C_2-C_6$ akanoyl; $C_{13}-C_{14}$ is ethylene or trans-vinylene; $R_7$ is a moiety selected from the group consisting of:

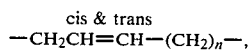

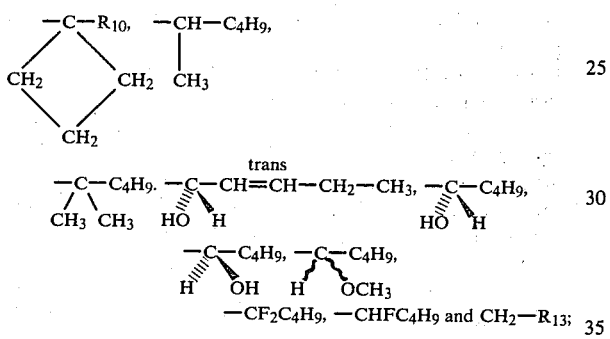

wherein $R_8$ is selected from the group consisting of $C_4-C_7$ alkyl, $C_5H_{11}$, cyclohexyl, cyclopentyl, wherein $R_9$ is selected from the group of $C_5H_{11}$,

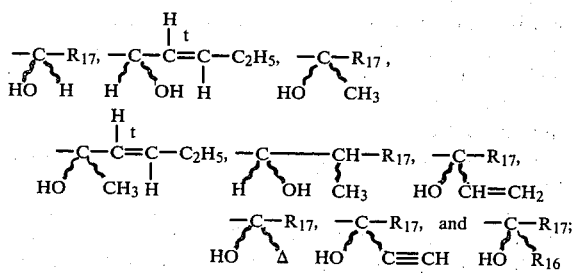

wherein $R_{16}$ is E-1-propenyl, Z-1-propenyl, and $R_{17}$ is $C_3-C_7$ alkyl; $R_{10}$ is selected from the group consisting of $-C_4H_9$,

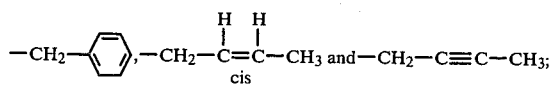

and $R_{13}$ is selected from the group consisting of phenyl, benzyl, phenoxy and phenoxy substituted by fluoro, chloro, trifluoromethyl or methyl, and when $R_{14}$ is hydroxy, the and pharmacologically acceptable cationic salts thereof. Compounds of the above formula wherein n is 3 and m is 4 are preferred.

A preferred class of compounds are the 15-deoxy-16-hydroxy-substituted prostanoic acids. The ring systems of these compounds are classified in accordance with the conventional prostaglandin types as follows:

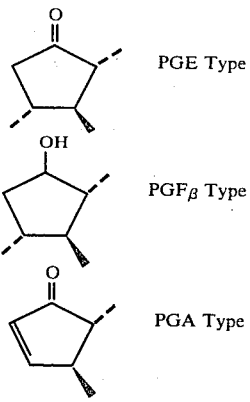

Synthetic analogs of the 16-hydroxy-16-substituted-PGE, PGF$_\beta$ and PGA types are represented by the following general formula and mirror image thereof:

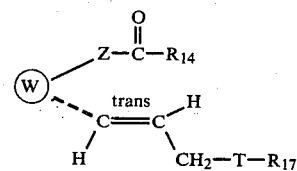

wherein W, Z, $R_{14}$, and $R_{17}$ are as hereinabove defined and T is the divalent radical:

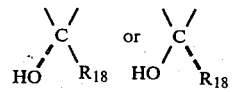

wherein $R_{18}$ is selected from the group comprising hydrogen, methyl, vinyl, methylvinyl, ethynyl and cyclopropyl. Compounds of the above formula wherein n is 3 and m is 4 are preferred.

16-hydroxy-16-substituted synthetic prostaglandin analogs are described in U.S. Pat. No. 4,061,670 which is incorporated by reference.

Synthetic prostaglandin derivatives of the 1-hydroxymethyl-1-oxo type are described in U.S. application Ser. No. 858,487 (filed Dec. 8, 1977) application now abandoned, which is incorporated by reference. This application discloses that the 1-hydroxymethyl-1-oxo-prostane derivatives of the E$_1$ series disclosed therein are useful as topical vasodilators.

Compounds employed by this invention are also described by U.S. Pat. No. 4,028,396, U.S. patent application Ser. Nos. 782,797, filed Mar. 30, 1977 now abandoned; 782,853 and 782,852, filed Mar. 30, 1977 U.S. Pat. No. 4,085,272 and now abandoned, respectively; 857,848, 857,849 and 857,714, filed Dec. 5, 1977 and now U.S. Pat. Nos. 4,190,596, 4,190,597 and 4,191,699 respectively; 858,589, 858,487, 858,588, 858,504, 858,580 and 858,579, filed Dec. 8, 1977 and now U.S. Pat. Nos. 4,202,822, application now abandoned, 4,170,597, 4,172,839, 4,197,245 and 4,212,769, respectively; which are incorporated by reference.

A 15-deoxy-16-hydroxy-16-substituted prostaglandin may consist of two dl racemates (16α-hydroxyl and 16β-hydroxyl) which, on occasion, are separable into the 16α and 16β epimers. A species claim wherein the stereochemistry of the $C_{16}$ carbon is not specified encompasses the optically active $16\alpha$ and $16\beta$ forms of the compound and the racemic mixtures thereof.

Useful pharmacologically acceptable salts of the above-described synthetic prostaglandins when $R_{14}$ is hydroxyl are those with pharmacologically acceptable metal cations, ammonium, amine cations or quarternary ammonium cations.

Preferred metal cations are those derived from the alkali metals, e.g., lithium, sodium and potassium, and from the alkaline earth metals, e.g., magnesium and calcium, although cationic forms of other metals, e.g., aluminum, zinc and iron, are within the scope of the invention.

Pharmacologically acceptable amine cations are those derived from primary, secondary or tertiary amines such as mono-, di- or triisopropylamine, N-methylhexylamine, decylamine, dodecylamine, allylamine, crotylamine, cyclopentylamine, dicyclohexylamine, allylamine, crotylamine, cyclopentylamine, dicyclohexylamine, mono- or dibenzylamine, $\alpha$- or $\beta$-phenylethylamine, ethylenediamine, diethylenetriamine, and arylaliphatic amines containing up to and including 18 carbon atoms, as well as heterocyclic amines, e.g., piperidine, morpholine, pyrrolidine, piperazine and lower alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, or triethanolamine, ethyldiethanolamine, N-butylethanolamine, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like.

Examples of suitable pharmacologically acceptable quarternary ammonium cations are tetramethylammonium, tetraethylammonium, benzyltrimethylammonium, phenyltriethylammonium and the like.

The term topical as employed herein means the application of the prostaglandin vasodilator to the surface of the skin in the area of the disease for the exertion of local action. The topical application of the prostaglandins disclosed herein may produce a distinct and persistent erythema which is restricted to the site of application when used in limited amounts. Since the activity of the prostaglandins of the instant invention when applied to the skin surface or by local injection is restricted to the site of application, the use of these compounds for the treatment of peripheral vascular diseases is preferable to the use of systemically active drugs disclosed by the prior art which are unable to produce a specific vasodilation in the critical arteriospastic or ischemic area.

The prostaglandin may also be administered in a carrier adapted for topical administration, such carriers include creams, ointments, lotions, pastes, jellies, sprays, aerosols, bath oils, or other pharmaceutical carriers which accomplish direct contact between the prostaglandin and the surface of the skin area to be treated. In general pharmaceutical preparations may comprise from about 0.001% to about 10%, and preferably from about 0.01 to 5% by w/w of the active prostaglandin in a suitable carrier. In some cases it may be necessary to dissolve the prostaglandin in an appropriate solvent such as ethanol or DMSO (dimethylsulfoxide) and the like to facilitate incorporation into a pharmaceutical preparation.

A concentration-response relationship has been noted for the topical preparations of the instant invention; that is, as the concentration of the prostaglandin in a given topical formulation is increased, for the same amount of the preparation administered, to the same total area of skin, the resultant vasodilation is intensified. Thus, the concentration of the active prostaglandin in the carrier, or the amount of the preparation applied may be adjusted to induce a localized vasodilation of the desired intensity.

The prostaglandins of the instant invention when topically applied may induce a distinct and persistent erythema at varying dosages. The erythema produced by some prostaglandins is more intense and persistent than for others. The amount of prostaglandin administered to produce a localized vasodilation of the desired degree will vary depending upon the particular prostaglandin employed, as well as the characteristics of the particular individual or disease to be treated. Thus, the topical formulation may be applied to the diseased area of the skin in one or more administrations per day and in amounts necessary to produce a localized vasodilation of the desired degree and persistence. In general, an effective dosage may represent from about 1 to 1000 $mg/m^2$ for the more active prostaglandins.

The localized administration of the effective prostaglandin may also be accomplished by injection. Injection refers to positioning a pharmaceutical preparation suitable for parenteral administration in the high dermis by needle or by high pressure air injection. The injectable compositions of the instant invention may also be administered intra- or peri-lesionally; that is by injection into the lesion or into the tissue immediately surrounding the lesion.

For administration by injection, fluid forms are prepared utilizing the active compound and a sterile vehicle, water being preferred when the composition is to be used immediately, i.e., not stored. The compound, depending on the form and concentration used, can be either suspended or dissolved in the vehicle. In preparing solutions, a water soluble form of the compound can be dissolved in water for injection and filter sterilized before transferring the solution into a suitable vial or ampule. Advantageously, adjuvants such as a local anesthetic, preservative and buffering agents can be dissolved in the vehicle. To enhance stability, the composition can be frozen within the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved, and sterilization cannot be accomplished by filtration. The compound can be sterilized before suspension in the sterile vehicle.

The effective dosage administered by injection at one or more sites to produce a localized or regional increase in circulation or to treat an ischemic area associated with a peripheral vascular disease comprises from about 0.001 to about 10 mg of the prostaglandin and preferably from about 0.003 to 2 mg per day. For the more active prostaglandins, however, such as 15-deoxy-16-hydroxy-16-vinyl-$PGE_2$ parenteral administrations of from about 0.002 to 0.2 mg per day constitutes an effective dosage. The degree to which the resultant effect is localized or generalized is determined by the amount and activity of the prostaglandin, and the number and distribution of injection sites.

Injectable compositions are prepared containing the prostaglandin in a pharmaceutical carrier suitable for parenteral administration in a concentration of from about 0.001 to 5%.

The following examples describe the manner and process of making and using the invention, but are not to be construed as a limitation thereon.

EXAMPLE 1

Topical Application of Prostaglandins under a Closed Dressing to the Arm and Back of a Human Test Subject Test solutions of 32 µg/ml, 320 µg/ml and 3.2 mg/ml of 15-deoxy-16-hydroxy-16-vinyl-$PGE_2$ and related prostaglandins in 15% ethanol-distilled water were prepared. 50 µl of the test solutions were applied on a gauze under a closed dressing to the arm of a human volunteer. The duration of contact was about two hours. The erythema induced was scored from 0 to + + + +. A score of 0 was recorded when no visible erythema was induced, and a score of + + + + when the erythema was intense. The results are summarized in Table I.

TABLE I

| | |
|---|---|
| A. Control: | (15% ethanol-85% distilled water) no visible erythema detected. |
| B. Prostaglandin: | 15-deoxy-16-hydroxy-16-vinyl-$PGE_2$ |
| 32 µg/ml: | 0 |
| 320 µg/ml: | + |
| 3.2 mg/ml: | + + (duration of effect 24 hours) |
| undiluted: | + + + (duration of effect 36 Hours) |
| C. Prostaglandin: | 1-hydroxymethyl-1,9-dioxo-16-methyl-11α, 16-dihydroxy-5-cis, 13-trans-prostadiene |
| 320 µg/ml: | + ⎫ (duration of effect 24 hours) |
| 3.2 mg/ml: | + + ⎭ |
| D. Prostaglandin: | 11-deoxy-11 (α and β)-2-hydroxyethylthio $PGE_2$ methyl ester. |
| 320 µg/ml: | 0 ⎫ |
| 3.2 mg/ml: | + ⎭ (duration of effect 24 hours) |

The following results summarized in Table II were observed upon application of the prostaglandin solution on gauze under a closed dressing to the back of a human test subject.

TABLE II

| | 32µg/ml | 320µg/ml | 3.2mg/ml | Undiluted |
|---|---|---|---|---|
| $PGE_2$, methyl ester | | | | |
| 2 hours | 0 | + | + + | + + + + |
| 24 hours | (0) | (0) | (0) | (0) |
| 15-deoxy-16-hydroxy-16-vinyl-$PGE_2$ | | | | |
| 2 hours | + + | + + + | + + + | + + + + |
| 24 hours | (0) | (+ +) | (+ +) | (0) |
| 1-hydroxymethyl-1,9-dioxo-16-methyl-11α, 16-dihydroxy-5-cis,-13-trans prostadiene | | | | |
| 2 hours | + | + + | + + | + + + |
| 24 hours | (0) | (0) | (0) | (0) |

EXAMPLE 2

Effects of Topically Applied All Racemic 15-Deoxy-16-Hydroxy-16-Vinyl-$PGE_2$ On Guinea Pig Skin Male albino guinea pigs, weighing 250 to 400 g were shaved and depilated on their flanks, the evening before testing, with a standard mixture of barium sulfide and gum acacia. On the day of testing all racemic 15-deoxy-16-hydroxy-16-vinyl-$PGE_2$ was dissolved at a concentration of 10 mg/ml in either DMSO or ethanol. Tenfold dilutions (1 mg/ml) of each were also prepared. Vehicle controls were DMSO or ethanol alone.

Three 3.5 cm diameter circles were drawn with a black marking pen on the flank of each guinea pig. Vehicle was applied to one of the circles and one (or two) concentrations of drug to the other circle by means of a cotton applicator stick (one swab). The amount of material deposited to the entire area within the circle was estimated by weighing the applicator stick after immersion in drug or vehicle and again after swabbing the guinea pig skin. Average amounts deposited were 11 mg (range 9–13 mg) for the ethanol and DMSO preparations.

Each circle was graded at 1, 2 and 24 hours after application of compound or vehicle according to the following:

0—no erythema
0.5—incomplete circle or faint erythema
1.0—complete circle of distinct erythema
2.0—intense erythema The effect of 15-deoxy-16-hydroxy-16-vinyl-$PGE_2$ on guinea pig skin is summarized in Table III.

TABLE III

| | TIME | | | | | | | | |
|---|---|---|---|---|---|---|---|---|---|
| | 1 hour | | | 2 hours | | | 24 hours | | |
| Treatment | A | B | C | A | B | C | A | B | C |
| A = 15-deoxy-16-hydroxy-16-vinyl-$PGE_2$ 10 mg/ml DMSO | | | | | | | | | |
| B = 15-deoxy-16-hydroxy-16-vinyl-$PGE_2$ 1 mg/ml DMSO | | | | | | | | | |
| C = DMSO | 0.6 | 0.4 | 0 | 0.9 | 0.5 | 0 | 0.4 | 0 | 0 |
| A = 15-deoxy-16-hydroxy-16-vinyl-$PGE_2$ 10 mg/ml ETOH | | | | | | | | | |
| B = 15-deoxy-16-hydroxy-16-vinyl-$PGE_2$ 1 mg/ml ETOH | | | | | | | | | |
| C = ETOH | | | | | | | | | |

EXAMPLE 3

Effect of Topically Applied All Racemic 15-Deoxy-16-Hydroxy-16-Vinyl-$PGE_2$ on Monkey Skin A female rhesus monkey (6.2 kg) was lightly anesthetized with 1 ml of Ketalar ®. Two adjacent rectangular areas of approximately 2 cm×3 cm on each forearm, abdomen and thigh were shaved. All racemic 15-deoxy-16-hydroxy-16-vinyl-$PGE_2$ in ethanol (10 mg/ml or 1 mg/ml) or ethanol alone was applied to each of the shaved areas of skin by means of a cotton applicator stick. Each entire area was swabbed twice, depositing approximately 0.030–0.060 ml of the solution. Each area was graded immediately after swabbing (time 0), and at 30, 60, 152, 270, 390 minutes for the degree of erythema according to the following:

0—no erythema
0.5—faint erythema
1.0—distinct erythema
2.0—intense erythema

Just prior to each of these readings an additional 0.5 ml of Ketalar ® was administered. The results are summarized in Table IV.

TABLE IV

Effect of Topically Applied All Racemic 15-deoxy-16-hydroxy-16-vinyl-PGE$_2$ on Rhesus Monkey Skin

| Spot[e] | | Concentration[a] | Timed Score[c] After Treatment (Minutes) | | | | | | |
|---|---|---|---|---|---|---|---|---|---|
| | | | 0 | 10 | 30 | 60 | 150 | 270 | 390 |
| A | Prostaglandin[d] | 10 mg/ml in ETOH | 0 | 0 | 0 | 0.5 | 1.0 | 0.5 | 0 |
| B | ETOH | | 0 | 0 | 0 | 0.5 | 0.5 | 0.5 | 0 |
| C | Prostaglandin[d] | 1 mg/ml in ETOH | 0 | 0.5 | 0.5 | 0.5 | 0.5 | 0 | 0 |
| D | ETOH | | 0 | 0 | 0 | 0 | 0 | 0 | 0 |
| E | Prostaglandin[d] | 10 mg/ml in ETOH | 0 | 0.5 | 0.5 | 0.5 | 0.5 | 0.5 | 0.5 |
| F | ETOH | | 0 | 0 | 0 | 0 | 0 | 0 | 0 |
| G | Prostaglandin[d] | 1 mg/ml in ETOH | 0 | 1.0 | 1.0 | 1.0 | 1.0 | 1.0 | 0.5[b] |
| H | ETOH | | 0 | 0 | 0 | 0 | 0 | 0 | 0 |
| I | Prostaglandin[d] | 10 mg/ml in ETOH | 0 | 0.5 | 1.0 | 1.0 | 2.0 | 2.0 | 2.0[b] |
| J | ETOH | | 0 | 0 | 0 | 0 | 0 | 0 | 0 |

[a]Amount of solution applied approximately 25–50 μl of 15-deoxy-16-hydroxy-16-vinyl-PGE$_2$ solution in stated solvent and at stated concentration.
[b]Increase in area size.
[c]Scoring: 0-no erythema, 0.5-faint erythema, 1.0-distinct erythema, 2.0-intense erythema.
[d]15-deoxy-16-hydroxy-16-vinyl-PGE$_2$.
[e]The spot positions are forearm (ABCD); thigh (EFGH) and abdomen (IJ).

EXAMPLE 4

Effect of Topically Applied 15-deoxy-16-hydroxy-16-vinyl-PGE$_2$ or the Methyl Ester thereof on Rabbit Ear Skin Temperature The dorsal ear surfaces of rabbits weighing approximately 4 kg were shaved. 15-Deoxy-16-hydroxy-16-vinyl-PGE$_2$ or the methyl ester thereof (approximately 80–100 μl of a 5 mg/ml ethanol solution) was applied to the entire dorsal surface of one ear and an equal volume of ethanol as a control was applied to the entire dorsal surface of the other ear.

Figure 2:
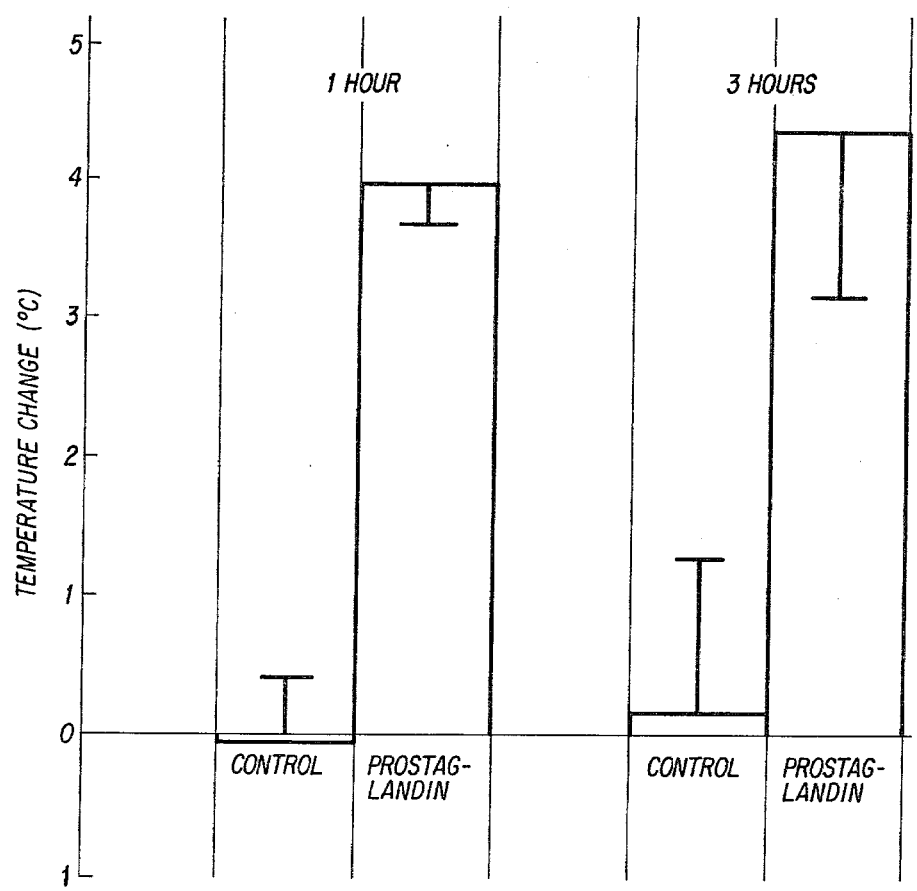

Skin temperatures were recorded on a Digital Thermistor thermometer (Digitec Model 5810) by means of a 709A surface probe. The probe was attached with a metal clip to the edge of the dorsal ear surface. In one experiment (FIG. 1) the temperature was monitored continuously from the same position on one ear, treated sequentially with ethanol and 15-deoxy-16-hydroxy-16-vinyl-PGE$_2$, 5 mg/ml in ethanol. In a second experiment (FIG. 2) the probe was shifted at specified times between corresponding positions on ethanol or prostaglandin (5 mg/ml in ethanol) treated ears of the same rabbit. In FIG. 2, skin temperatures were recorded before and 1 and 3 hours after application. Mean temperature changes (before vs. after) produced by the prostaglandin solution or ethanol control are presented in FIG. 2 along with the standard error of the mean. Statistical comparison of means by Student's Test indicates that the temperature effects of the prostaglandin compared to those of the control are significant at $P<0.05$. The results of these experiments are summarized in FIGS. 1 and 2 below; wherein temperature is assumed to be a reflection of vasodilation and blood flow.

EXAMPLE 5

Injectable Formulations

A sterile aqueous solution for injection containing in 1 cc. 10 mg of the prostaglandins of the instant invention is prepared from the following types and amounts of materials:

| | |
|---|---|
| Prostaglandin | 10 gm |
| Lidocaine hydrochloride | 4 gm |
| Methylparaben | 2.5 gm |
| Propylparaben | 0.17 gm |
| Water for injection q.s. | 1000 cc |

The ingredients are dissolved in the water and the solution sterilized by filtration. The sterile solution is poured into vials and the vials sealed. The composition is to be used immediately.

EXAMPLE 6

Injectable Formulations

A sterile aqueous solution for injection containing in 1 cc 1 mg of the prostaglandins of the instant invention, as the Na salt, is prepared from the following types and amounts of ingredients:

| | |
|---|---|
| Prostaglandin | 1 gm |
| Sodium chloride 10% solution q.s. | |
| Water for injection q.s. | 1000 cc |

Prostaglandin is added to the water and sufficient sodium chloride added to form an isotonic solution and the solution sterilized by filtration. The sterile solution is used immediately and injected intradermally by high pressure injection for the treatment of peripheral vascular diseases.

EXAMPLE 7

Parenteral grade prostaglandin is dissolved in anhydrous N,N-dimethylacetamide containing 0.4% water (determined by the Karl Fischer Method) in the proportions of 5 mg of the prostaglandin for each ml of anhydrous N,N-dimethylacetamide. The solution is then filter sterilized by passing it through a microporous (solvent-resistant) filter, e.g., Millipore Solvinert, 0.25 microns, or Gelman Metricel Alpha-8, 0.2 microns, aseptically packaged in 1 ml quantities in sterile ampuls and kept under refrigeration at not more than 5° until needed. At that time the contents of one ampul (1 ml) are diluted into 1 liter of infusion solution and administered by high pressure injection, intradermally for the treatment of peripheral vascular disorders of the arteriospastic and occlusive types.

EXAMPLE 8

The formulations of Examples 5–7 are administered by local injection to an ischemic area of the skin for the treatment of peripheral vascular disorders of the occlusive or arteriospastic types.

EXAMPLE 9

The compositions of Examples 5–7 can similarly be employed to treat Raynaud's phenomenon, Raynaud's disease, Buerger's disease, Livedo Reticulars acrocyanosis, atherosclerosis, frostbite, vitiligo, alopecia areata, psoriasis, atopic dermatitis, acne and impending gangrene.

EXAMPLE 10

Additional prostaglandins for use in this invention, and for formulation with a pharmaceutical carrier are listed below in Table V. These may be formulated and applied topically.

TABLE V 11-deoxy-16-p-fluorophenoxy-17,20-tetranor $PGE_2$ and esters
11-dexoy-16,20-methano $PGE_1$ and esters
11-deoxy-16,20-methano $PGE_2$ and esters
11-deoxy-16,19-methano-20-nor-$PGE_1$ and esters
11-deoxy-16,19-methano-20-nor-$PGE_2$ and esters
16-fluoro $PGE_1$ and esters
11,15-bisdeoxy-16- hydroxy-17-methyl $PGE_1$
11-deoxy-16,16-trimethylene-17-phenyl-18,20-trinor-$PGE_2$ and esters
11-deoxy-16-p-chlorophenoxy-17,20-tetranor $PGE_1$ and esters
11-deoxy-16-p-chlorophenoxy-17,20-tetranor $PGE_2$ and esters
11-deoxy-16-p-fluorophenoxy-17,20-tetranor $PGE_1$ and esters
15(S)-15-methyl $PGE_2$ and esters
15(R)-15-methyl $PGE_2$ and esters
15(S)-15-methyl $PGE_1$ and esters
15(R)-15-methyl $PGE_1$ and esters
16,16-dimethyl $PGE_1$ and esters
16,16-dimethyl $PGE_2$ and esters
16,16-trimethylene $PGE_1$ and esters
16,16-trimethylene $PGE_2$ and esters
16,16-trimethylene-18-yne $PGE_1$ and esters
16,16-trimethylene-cis-18-ene-$PGE_1$ and esters
16,16-trimethylene-18-yne $PGE_2$ and esters
16,16-trimethylene-cis-18-ene $PGE_2$ and esters
16,16-trimethylene-17-phenyl-18,20-trinor-$PGE_1$ and esters
16,16-trimethylene-17-phenyl-18,20-trinor-$PGE_2$ and esters
16-methyl $PGE_1$ and esters
16-methyl $PGE_2$ and esters
16-methylene $PGE_1$ and esters
16-methylene $PGE_2$ and esters
erythro 16-hydroxy $PGE_1$ and esters
erythro 16-hydroxy $PGE_2$ and esters
ehreo 16-hydroxy $PGE_1$ and esters
ehreo 16-hydroxy $PGE_2$ and esters
erythro 16-hydroxy-trans-17-ene $PGE_1$ and esters
erythro 16-hydroxy-trans-17-ene-$PGE_2$ and esters
erythro 16-methoxy $PGE_1$ and esters
threo 16-methoxy $PGE_1$ and esters
threo 16-methoxy $PGE_2$ and esters
16,16-difluoro $PGE_1$ and esters
16,16-difluoro $PGE_2$ and esters
16-fluoro $PGE_2$ and esters
16-phenyl-17,20-tetrano $PGE_1$ and esters
16-phenyl-17,20-tetranor $PGE_2$ and esters
17-phenyl-18,20-trinor $PGE_1$ and esters
17-phenyl-18,20-trinor $PGE_2$ and esters
16-phenoxy-17,20-tetranor $PGE_1$ and esters
16-phenoxy-17,20-tetranor $PGE_2$ and esters
16-m-trifluoromethyl phenoxy 17,20-tetranor $PGE_1$ and esters
16-m-trifluoromethyl phenoxy 17,20-tetranor $PGE_2$ and esters
16-p-chlorophenoxy-17,20-tetranor $PGE_1$ and esters
16-p-chlorophenoxy-17,20-tetranor $PGE_2$ and esters
16-p-fluorophenoxy-17,20-tetranor $PGE_1$ and esters
16-p-fluorophenoxy-17,20-tetranor $PGE_2$ and esters
16,20-methano $PGE_1$ and esters
16,20-methano $PGE_2$ and esters
16,19-methano-20-nor-$PGE_1$ and esters
16,19-methano-20-nor $PGE_2$ and esters
15-deoxy-$PGE_1$ and esters
15-deoxy-$PGE_2$ and esters
15-deoxy-16-hydroxy $PGE_1$ and esters
B 15-deoxy-16-hydroxy $PGE_2$ and esters
15-deoxy-16(S)-hydroxy $PGE_1$ and esters
15-deoxy-16(R)-hydroxy $PGE_1$ and esters
15-deoxy-16-hydroxy-trans-17-ene $PGE_2$ and esters
15-deoxy-16-hydroxy-16-methyl $PGE_1$ and esters
15-deoxy-16-hydroxy-16-methyl $PGE_2$ and esters
15-deoxy-16-hydroxy-16-methyl-trans-17-ene $PGE_2$ and esters
15-deoxy-16-hydroxy-16-vinyl $PGE_1$ and esters
15-deoxy-16-hydroxy-16-vinyl $PGE_2$ and esters
15-deoxy-16-hydroxy-17-methyl $PGE_2$ and esters
11,15 bisdeoxy-16-hydroxy $PGE_1$ and esters
11,15 bisdeoxy-16-hydroxy $PGE_2$ and esters
11,15 bisdeoxy-16(S)-hydroxy $PGE_1$ and esters
11,15 bisdeoxy-16(R)-hydroxy $PGE_1$ and esters
11,15 bisdeoxy-16-hydroxy-trans-17-ene $PGE_1$ and esters
11,15 bisdeoxy-16-hydroxy-trans-17-ene $PGE_2$ and esters
11,15 bisdeoxy-16-hydroxy-16-methyl $PGE_1$ and esters
11,15 bisdeoxy-16-hydroxy-16-methyl $PGE_2$ and esters
11,15 bisdeoxy-16-hydroxy-16-methyl-trans-17-ene $PGE_1$ and esters
11,15 bisdeoxy-16-hydroxy-B 16-methyl-trans-17-ene $PGE_2$ and esters
11,15 bisdeoxy-16-hydroxy-16-vinyl $PGE_1$ and esters
11,15 bisdeoxy-16-hydroxy-16-vinyl $PGE_2$ and esters
11,15 bisdeoxy-16-hydroxy-17-methyl $PGE_1$ and esters
11,15 bisdeoxy-16-hydroxy-17-methyl $PGE_2$ and esters
11-deoxy-15(S)-15-methyl $PGE_2$ and esters
11-deoxy-15(R)-15-methyl $PGE_2$ and esters
11-deoxy-15(S)-15-methyl $PGE_1$ and esters
11-deoxy-15(R)-15-methyl $PGE_2$ and esters
11-deoxy-16,16-dimethyl $PGE_1$ and esters
11-deoxy-16,16-dimethyl $PGE_2$ and esters
11-deoxy-16,16-trimethylene $PGE_1$ and esters
11-deoxy-16,16-trimethylene $PGE_2$ and esters
11-deoxy-16,16-trimethylene-18-yne $PGE_1$ and esters 11-deoxy-16,16-trimethylene-18-ene-PGE$_1$ and esters
11-deoxy-16,16-trimethylene-18-yne PGE$_2$ and esters
11-deoxy-16,16-trimethylene-cis-18-ene and esters
11-deoxy-16-methyl PGE$_1$ and esters
11-deoxy-16-methyl PGE$_2$ and esters
11-deoxy-16-methylene PGE$_1$ and esters
11-deoxy-16-methylene PGE$_1$ and esters
11-deoxy erythro 16-hydroxy PGE$_1$ and esters
11-deoxy erythro 16-hydroxy PGE$_2$ and esters
11-deoxy threo 16-hydroxy PGE$_1$ and esters
11-deoxy threo 16-hydroxy PGE$_2$ and esters
11-deoxy erythro 16-hydroxy-trans-17-ene PGE$_1$ and esters
11-deoxy erythro 16-hydroxy-trans-17-ene-PGE$_2$ and esters
11-deoxy erythro 16-methoxy PGE$_1$ and esters
11-deoxy erythro 16-methoxy PGE$_2$ and esters
11-deoxy threo 16-methoxy PGE$_1$ and esters
11-deoxy threo 16-methoxy PGE$_2$ and esters
11-deoxy 16,16-difluoro PGE$_1$ and esters
11-deoxy 16,16-difluoro PGE$_2$ and esters
11-deoxy 16-fluoro PGE$_1$ and esters
11-deoxy 16-fluoro PGE$_2$ and esters
11-deoxy 16-phenyl-17,20-tetranor PGE$_1$ and esters
11-deoxy 16-phenyl-17,20-tetranor PGE$_2$ and esters
11-deoxy 17-phenyl-18,20-trinor PGE$_1$ and esters
11-deoxy 17-phenyl-18,20-trinor PGE$_2$ and esters
11-deoxy-16-phenoxy-17,20-tetranor PGE$_1$ and esters
11-deoxy-16-phenoxy-17,20-tetranor PGE$_2$ and esters
11-deoxy-16-m-trifluoromethyl phenoxy 17,20-tetranor PGE$_1$ and esters
11-deoxy-16-m-trifluoromethyl phenoxy 17,20-tetranor PGE$_2$ and esters
16,16-dimethyl-$\Delta^2$-trans-PGE$_1$
prostacyclin
prostacyclin sodium salt
6$\beta$-PGI$_1$ or 5-Iodo-6$\beta$-PGI$_1$

EXAMPLE 11

Topical Application of 320 μg/ml and 3.2 mg/ml Ethanol-Water Solutions of PGE$_1$, PGA$_2$ and PGF$_{2\beta}$ Test solutions of natural prostaglandin compounds PGE$_1$, PGA$_2$ and PGF$_{2\beta}$ in 15% ethanol-distilled water are prepared at concentrations of 320 μg/ml and 3.2 mg/ml. 50 μl of the solution was applied on a gauze under a closed dressing in accordance with the procedure of Example 1 to the arm of a human test subject. The duration of contact was about 2 hours. No visible erythema was produced.

EXAMPLE 12

Administration of Prostaglandin Derivatives by Injection to Test Animals

50 μl test solutions of 320 μg/ml concentrations of PGE$_2$ methyl ester, 1-hydroxymethyl-1,9-dioxo-16-methyl-11α,16-dihydroxy-5-cis,13-trans-prostadiene, and 15-deoxy-16-hydroxy-16-vinyl-PGE$_2$ were prepared. Each of the solutions was administered by intradermal injection to the skin of a rabbit, 10 rats and 2 guinea pigs. The solutions were also applied directly to the surface of the skin of 10 rabbits. No clear erythema was induced by either the intradermal injection or the epicutaneous contact.

EXAMPLE 13

Intradermal Injection of 15-Deoxy-16-Hydroxy-16-Vinyl-PGE$_2$ and 1-Hydroxy-Methyl-1,9-Dioxo-16-Methyl-11α,16-Dihydroxy-5-Cis,13-Trans-Prostadiene.

During a Pilocarpine test for bronchodilator activity, a test dog was injected with 50 μl of a 3.2 mg/ml solution of 15-deoxy-16-hydroxy-16-vinyl-PGE$_2$ in a 15% ethanol-water carrier. A general erythema was observed which was very marked at the point of injection. A marked effect was also noted on the following parameters:
  decrease of resistance
  tachycardy
  increase in pulmonary arterial pressure
  decrease in femoral arterial pressure.

50 μl of a 3.2 mg/ml solution of 1-hydroxymethyl-1,9-dioxo-16-methyl-11α,16-dihydroxy-5-cis,13-trans-prostadiene in a 15%-ethanol-water carrier was also injected intradermally into a test dog during a Pilocarpine test. A general erythema was produced which was very marked at the point of injection. No effect was observed however, on the resistance, pulmonary arterial pressure, or femoral arterial pressure.

EXAMPLE 14

PGE$_2$ methyl ester, 1-hydroxymethyl-1,9-dioxo-16-methyl-11α,16-dihydroxy-5-cis,13-trans-prostadiene, and 15-deoxy-16-hydroxy-16-vinyl-PGE$_2$ were inhaled by six human volunteers. 15-Deoxy-16-vinyl-PGE$_2$ at a dosage of about 120 μg induced a facial flush in three of the six volunteers. A facial flush was not observed for the other compounds tested.

EXAMPLE 15

Topical Formulations

The following compounds may be formulated for topical applications in a 15% ethanol in distilled water solution:

TABLE VI 9-oxo-11α,16-dihydroxy-16-vinyl-5-cis,13-trans prostadienoic acid 1-PGE$_2$
15-deoxy-16-hydroxy-PGE$_2$ methyl ester
15-deoxy-16-hydroxy-16-methyl-17-trans-PGE$_2$
15-deoxy-16-hydroxy-16-methyl-PGE$_2$
15-deoxy-16-hydroxy-16-vinyl-PGE$_2$ methyl ester
1,9-dioxo-1-hydroxymethyl-11α,16-dihydroxy-16-vinyl-13-trans-prostene
9-oxo-11α,16-dihydroxy-16-vinyl-20-nor-5-cis,13-trans-prostadienoic acid
1,9-dioxo-1-hydroxymethyl-11α,16-dihydroxy-16-vinyl-5-cis,13-trans-prostadiene
9-oxo-11α,16-dihyroxy-16-ethynyl-5-cis,13-trans-prostadienoic acid
1,9-oxo-1-hydroxymethyl-11α,16-dihydroxy-16-ethyl-5-cis,13-trans-prostadiene.
9-oxo-11α,16-dihydroxy-16-vinyl-20-ethyl-5-cis,13-trans-prostadienoic acid
9-oxo-11α,16-dihydroxy-16-cyclopropyl-5-cis,13-trans-prostadienoic acid
9-oxo-11α,16-dihydroxy-16-vinyl-20-methyl-5-cis,13-trans-prostadienoic acid
9-oxo-11α,16-dihydroxy-16-(2-propenyl)-5-cis,13-trans-prostadienoic acid 9-oxo-11α,16-dihydroxy-13-trans,17-trans-prostadienoic acid This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed products are considered to be within the purview and scope of this invention and the following claims.

I claim:

1. A method for producing an increase in local cutaneous and deep vessel circulation for individuals suffering from peripheral vascular disease of the arteriospastic and occlusive types which comprises topically administering to an individual suffering from said peripheral vascular disease an effective amount of a compound of the formula:

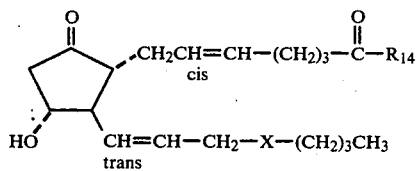

or a racemic mixture of that formula and the mirror image thereof wherein X is

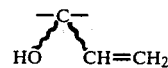

and $R_{14}$ is selected from the group consisting of hydroxyl, $C_1$-$C_6$ alkoxy, —$CH_2OH$ and —$CH_2OR_{15}$ wherein $R_{15}$ is $C_2$-$C_6$ alkanoyl, and when $R_{14}$ is hydroxy, the pharmacologically acceptable cationic salts thereof.

2. The method according to claim 1 wherein $R_{14}$ is hydroxyl.

3. The method according to claim 1 wherein $R_{14}$ is —$CH_2OH$.

4. The method according to claim 1 wherein $R_{14}$ is —$CH_2OR_{15}$.

5. The method according to claim 1 wherein $R_{14}$ is $C_1$-$C_6$ alkoxy.

6. The method in accordance with claim 1 wherein said compound is 9-oxo-11α,16-dihydroxy-16-vinyl-5-cis,13-trans-prostadienoic acid.

7. The method according to claim 1 wherein said compound is methyl 9-oxo-11α,16-dihydroxy-16-vinyl-5-cis,13-trans prostadienoate.

8. The method according to claim 1 wherein said compound is 1,9-dioxo-1-hydroxymethyl-11α,16-dihydroxy-16-vinyl-5-cis,13-trans-prostadiene.

9. The method according to claim 1, wherein the effective dosage comprises from about 1 to 1000 mg/m².

* * * * *